United States Patent [19]
Goldreyer

[11] Patent Number: 5,579,764
[45] Date of Patent: *Dec. 3, 1996

[54] METHOD AND APPARATUS FOR SPATIALLY SPECIFIC ELECTROPHYSIOLOGICAL SENSING IN A CATHETER WITH AN ENLARGED ABLATING ELECTRODE

[76] Inventor: Bruce N. Goldreyer, 30311 Palos Verdes Dr. East, Rancho Palos Verdes, Calif. 90275

[*] Notice: The term of this patent shall not extend beyond the expiration date of Pat. No. 5,450,846.

[21] Appl. No.: 450,986

[22] Filed: May 25, 1995

Related U.S. Application Data

[63] Continuation-in-part of Ser. No. 177,880, Jan. 5, 1994, Pat. No. 5,450,846, which is a continuation-in-part of Ser. No. 1,980, Jan. 8, 1993, Pat. No. 5,385,146.

[51] Int. Cl.$^6$ ..................................................... A61B 5/04
[52] U.S. Cl. ............................................. 128/642; 607/122
[58] Field of Search ................................... 128/642, 639, 128/695 R; 606/32; 607/100, 101, 115, 116, 119, 122, 154, 123, 124

[56] References Cited

U.S. PATENT DOCUMENTS

| | | | |
|---|---|---|---|
| 4,945,912 | 8/1990 | Langberg | 128/642 |
| 5,228,442 | 7/1993 | Imran | 128/642 |
| 5,450,846 | 9/1995 | Goldreyer | 128/642 |

FOREIGN PATENT DOCUMENTS

| | | | |
|---|---|---|---|
| 49212 | 12/1992 | WIPO | 128/642 |

*Primary Examiner*—Angela D. Sykes
*Assistant Examiner*—Bryan Yarnell
*Attorney, Agent, or Firm*—Daniel L. Dawes

[57] ABSTRACT

Orthogonal sensors, which are comprised of two or more electrodes and generally disposed circumferentially on the catheter at given longitudinal point along the catheter, receive signals which are differenced within a differential amplifier to produce a signal indicative only of the localized biopotential heart activity at a predetermined point in the myocardium. The orthogonal sensors are disposed in an ablative tip of the catheter to allow sensing of the localized cardiac activity which is adjacent to or in contact with the ablative tip during extirpation procedure or during the delivery of radio frequency energy during ablation. Sensing of the localized cardiac activity occurs simultaneously either with the ablation so that detailed and accurate electrocardiograms of the very tissue being ablated can be recorded.

11 Claims, 9 Drawing Sheets

METHOD AND APPARATUS FOR SPATIALLY SPECIFIC ELECTROPHYSIOLOGICAL SENSING IN A CATHETER WITH AN ENLARGED ABLATING ELECTRODE

RELATED APPLICATIONS

The present application is a continuation-in-part application of the application filed on Jan. 5, 1994, Ser. No. 08/177,880, entitled METHOD FOR SPATIALLY SPECIFIC ELECTROPHYSIOLOGICAL SENSING FOR MAPPING, PACING AND ABLATING HUMAN MYOCARDIUM AND A CATHETER FOR THE SAME now issued as U.S. Pat. No. 5,450,846, which in turn is a continuation-in-part application of application Ser. No. 08/001,980 filed Jan. 8, 1993 now issued as U.S. Pat. No. 5,385,146.

BACKGROUND OF THE INVENTION

1. Field of the Invention

The invention relates to the field of electrophysiology and more particularly to the sensing of extremely localized intracardiac electrical patterns in an ablating catheter.

2. Description of the Prior Art

The prior focus of electrophysiology has been directed to identifying the mechanisms of heart arrhythmias and evaluation of drug and other therapies upon the observed arrhythmias. Current studies in electrophysiology have continued to evolve by identifying localized areas of abnormal myocardium as the sources of arrhythmias and to selectively remove or otherwise deactivate the abnormal myocardium. Obliteration has generally been practiced through localized ablation, generally using a short range radio frequency diathermy technique, although other energy sources such as laser energy, ultrasound and/or cyroprecipitation may also be used.

The treatment of heart arrhythmias has thus become increasing dependent upon the ability to identify the precise anatomic location or origin in the myocardium of the abnormal rhythms. The prior art practice for locating the abnormal myocardium is to dispose a catheter within the heart chamber carrying a standard array of ring and tip electrodes. Direct contact of the tip electrode is used for making an intracardiac electrogram in a manner similar to that which has been practiced for many years with respect to pacemaker sensing. See, Imran, *"Endocardial Mapping and Ablation System and Catheter Probe"*, U.S. Pat. No. 5,156,151 (1992).

Consider the teachings of the prior art with respect to mapping local cardiac signals, and sensing the very tissue which is being stimulated by the pacing pulse or being ablated. Goldreyer, *"Method and Probe for Sensing Intracardiac Signals,"* Canadian Patent 1,192,263 is a 1985 patent by the applicant directed to a method and probe for sensing signals within the heart for the purposes of making EKG's and does not specifically address mapping, or ablation. Goldreyer, Canadian '263 teaches a method for sensing heart activity corresponding to a depolarization vector in the heart in terms of sensing local cardiac signals on orthogonal electrodes. The teaching is also directed to providing a ventricular pacing signal upon verification of existence of certain discriminatorily sensed local cardiac signals elsewhere in the heart, primarily in the atrium. The step of sensing does not expressly contemplate sensing from the precise area being paced; Goldreyer specifically teaches that such sensing shall be from areas removed spatially from the location of pacing. The possibility of simultaneously sensing localized cardiac activity specifically from the precise tissue where a stimulating pulse is being applied via the same catheter or sensing electrical activity from tissue while simultaneously applying ablative energy through the catheter tip to the sensed area is not implicitly or explicitly addressed nor motivated in any sense by Goldreyer, Canadian '263.

One of the reasons for lack of motivation from Goldreyer, Canadian '263 with such simultaneous steps of sensing and pacing or ablating, is that the signal strength received by the local cardiac signals is derived only from tissue near the orthogonal electrodes. The sensed area is small and the electrical signal generated by the sensed area is correspondingly weak. The very strong pacing or ablating signal energy was thought to completely swamp out the weak sensed local cardiac signal in any type of detection circuitry capable of sensing both.

In conventional catheters, such as catheters having ring electrodes, the electronics coupled to the sensing electrodes are turned off or the signal received by them is simply ignored during the time in which the pacing or ablating signal occurs. If the sensing electrodes are not electrically disconnected from the sense amplifier during the pacing or ablating phase, the sense amplifier is saturated and requires that a substantial recovery time before it can again sense signals of the magnitude generated by the local myocardium. The result is that signals during this recovery phase are simply missed.

The situation is similar in concept to radio transmissions in which the receiver and transmitter share the same antenna in a transceiver. When the transmitter is broadcasting, the receiver portion of the transceiver is disconnected from the antenna so that it is not swamped or saturated by the strong transmitting signal. Only after the transmitting signal is off, does electronic switch reconnect the radio receiver to the antenna so that the dramatically weaker received signals can be heard.

Second, even if Goldreyer, Canadian '263 is read as motivating the sensing of signals while pacing or ablating elsewhere in the heart, it must be recognized that Goldreyer, Canadian '263 actually teaches sensing in the atrium or at least a meaningful distance away from the pacing tip. None of the Figures in Goldreyer, Canadian '263 show the orthogonal sensing electrodes anywhere near the pacing tip, i.e. within a few millimeters of the pacing tip. It must be recognized that blood is an extremely lossy medium to high frequency electromagnetic waves. It is in essence sea water which is well known to be highly opaque to radio emissions. It is for this reason that it is impossible, for example, to detect submarines by radar or for submarines to communicate through radio transmissions with other stations unless an antenna is surfaced.

Therefore, even if Goldreyer, Canadian '263 can be understood to motivate simultaneous sensing and pacing, a position which the applicant firming rejects, it is by no means obvious even in hindsight that simultaneous sensing could be obtained if the orthogonal electrodes are very close the pacing or ablating tip. In Goldreyer, Canadian '263 the sensing electrodes are far enough from the pacing tip that the loss incurred in the blood between the tip and electrodes is large enough that substantial attenuation of the pacing pulse at the relatively distant electrodes might be expected. This leaves unanswered the question of whether the orthogonal electrodes could still sense local myocardial signals if they were proximate to the pacing or ablating tip. Based on Goldreyer, Canadian '263, the outcome of such an experiment could not be predicted.

Jackman et al., "New Catheter Technique for Recording Left Free-Wall Accessory Atrioventricular Pathway Activation Identification of Pathway Fiber Orientation," Circulation, Part 1, Volume 78, Number 3, September 1988, describes an application of an orthogonal sensor in the coronary sinus on the exterior of the surface of the heart. Orthogonal sensors A, B and C are shown in FIG. 1 have large scale separations of 10 millimeters. As stated in the right column at page 599, the catheter was advanced into the coronary sinus and positioned as anteriorly as possible in the great cardiac vein. Electrograms from the electrodes were examined to identify which electrodes faced the myocardium. Certain ones of electrodes, i.e. the half rings, were then identified as being closest to the heart tissue.

All sensing described by Jackman was conducted solely in the coronary sinus and great cardiac vein. The catheter was never placed within the heart and it does not appear that the use of the orthogonal probes in the catheter within the heart occurred to Jackman.

Further, it does not appear that Jackman conducted either any pacing or ablation while attempting to simultaneously sense local myocardial signals with the orthogonal electrodes. In fact, the catheter shown in Jackman contained no tip electrode capable of either pacing or the application of ablative energy. The purpose of the Jackman study was an attempt to locate and trace the Kent bundles and accessory pathways on the outside of the heart and not to discriminatorily sense or pinpoint malfunctioning myocardial tissue inside the heart. Being able to sense electrical activity on the outside of the heart wall is a prior art technique which does not include, contemplate or motivate myocardial mapping or selective ablation deep in the interior heart tissues. Nor does this technique teach localized sensing during the application of ablative energy.

Jackman describes the orthogonally spaced electrodes, but does not explicitly describe any differential amplification of the signals from the electrode pairs, nor local sensing of the heart signals.

Furthermore, the orthogonal electrodes are actually split rings and not dot or microelectrodes. Jackman does not monitor a differential signal between the ring electrode halves, but examines "the electrode facing the myocardium," namely that electrode or portion of the split ring facing the myocardium. There is no motivation, suggestion or teaching in Jackman, which would suggest that closely spaced bipolar differentially amplified electrodes can be used for mapping local myocardial signals inside the heart or simultaneously used for sensing during pacing or ablation.

Hess et al., "Percutaneous Lead Having Radially Adjustable Electrode," U.S. Pat. No. 4,660,571 (1987) describes a lead which is provided for the endocardial functions of mapping, ablation and/or pacing. Elongated electrodes on the distal end of the catheter are moved radially outward to provide a plurality of radially adjustable contact electrodes for the purposes of mapping. An electrode is provided on the tip also for ablation and pacing. Hess shows what is a conventional spring or spider array of contact electrodes in FIGS. 3 and 4 which are disposed outwardly to physically contact the heart wall. Not only is the position of these electrodes difficult to control, but they also tend to be spaced apart by a minimum predetermined distance as determined by the extent of radial splay of the flexible fingers 32 from the end of the catheter shown in FIG. 1 in the nondeployed configuration and in the deployed configuration in FIGS. 3 and 4.

What Hess describes, in particular beginning at column 6, lines 15–60, is a mapping or positioning of the electrode within the heart through the use of the contact electrodes and thereafter ablating the endocardial site where the abnormal focus has been located. There is no suggestion, teaching, motivation or claim made by Hess that he is able to continue sensing the local myocardial site which is being subject to ablation. Instead, Hess teaches a two-step process in which the abnormal focus is located, and once located then ablated. Hess does not employ orthogonal electrodes, nor describes, nor addresses the problem of how to avoid saturating his sensing electronics during the strong radiofrequency ablation. This was not even a problem which concerned Hess since he did not use radio frequency energy to ablate, but used a laser power source through an optical fiber as the ablating element. The suggestion at column 7, lines 1–14, that sensing and pacing may also be performed, is not described as being simultaneous, does not address the problem of sense amplifier saturation, and does not describe differential amplification of the electrode signals. Hess' suggestion that control of dysrythmia by pacing the ventricle merely suggests the use of the tip electrode 37 and ring electrode 47 as a bipolar electrode pair and does not address how the pacing electrodes can be simultaneously used with other sensing electrodes and in close proximity to each other so that the localized myocardium, which is being paced, can be simultaneously sensed. There is nothing in Hess which suggests that this could even be done. It was the conventional wisdom at the time of Hess, in fact, that this could not be done and it has only been shown on the basis of applicant's teaching that it is possible.

One of the recognized problems in prior art pacemaking has been the ability to simultaneously monitor the activity within the heart chamber while a large ventricular stimulating pulse was delivered through the catheter tip. One prior art solution is shown in Goldreyer, "Catheter, Cardiac Pacemaker and Method of Pacing", U.S. Pat. No. 4,365,639 (1982), wherein orthogonal sensing electrodes positioned on the catheter in the atrium were able to sense heart activity without being overwhelmed or saturated by the large ventricular stimulating pulse delivered through the catheter tip. In other words, because of the orthogonal placement of the sensing electrodes within the catheter body relative to the stimulating tip and the differential signal processing from the orthogonal electrodes, signals in the heart from directions other than the tip of the catheter could be preferentially sensed shortly after the large pacing and responsive ventricular pulse without saturation of the sensing circuitry. However, even in this prior art technology it was believed necessary to distance the sensing electrodes from the pacing tip by what is considered in terms of the present invention to be a large distance, namely 10 to 16 cm. See column 4, lines 41–42. It was not known or understood that the very tissue being paced could also be simultaneously sensed. What was being sensed was tissue far away from the site of stimulation, 10–16 cm away, which was not responding to the pacing spike, but to the heart propagation wave.

Electrophysiology has gone from an era where the purpose was the evaluation of the mechanisms or arrhythmias and evaluation of drug therapy to one which involves the localization of areas of abnormal myocardium in order to remove or obliterate them. In this regard, the mapping of the precise origin of the abnormal rhythms is extremely important. In the prior art, standard ring electrodes are placed on the catheter and the catheter moved within the cardiac chambers in an attempt to find the tissue spot which depolarized first and was the focus of the arrhythmia. Such probes have been of some use to spatially identify points in the myocardium having particular electrophysiological activity, however, signals derived from this standard electrode array suffer from considerable far-field influences and lack precise localization for accurate mapping purposes.

In clinical electrophysiology, recent studies have stressed that the localization of the site from which abnormal rhythms originate may be confirmed by pacing from the mapped area and demonstrating that the surface activation is identical to that seen during the spontaneous arrhythmia. Using standard ring electrodes as is currently done, intracardiac electrograms cannot be simultaneously recorded from the site of stimulation during these pacing sequences. This can be achieved by the invention.

What is needed is a method and apparatus for reliably mapping discrete electrophysiologic activity in the heart without the need to contact the heart walls and which sensing from the localized myocardium can be done simultaneously with pacing or ablation procedures from the precise tissue being stimulated.

BRIEF SUMMARY OF THE INVENTION

The invention is an ablating catheter for ablation of myocardium in a human heart comprising a catheter body for disposition within the heart. The catheter body has a distal tip. An ablative electrode is disposed on the distal tip. At least one pair of orthogonal electrodes is disposed in the ablative electrode and is electrically insulated therefrom. The electrodes receive electrocardiac signals only from a localized area within the myocardium, which area is ablated. A circuit differences the cardiac signals received by the at least one pair of orthogonal electrodes to generate an electrographic signal indicative of localized cardiac activity at the area. As a result, the catheter is usable for ablating and sensing electrophysiologic activity of the ablated myocardium without any limitation of size of the ablative electrode.

The orthogonal electrodes may simultaneous sense electrophysiologic activity at a predetermined point where in the myocardium is being ablated or may sense electrophysiologic activity at another point nearby or distant.

In the illustrated embodiment the orthogonal electrodes are disposed in the ablative electrode within 1 to 5 millimeters from the distal tip. The ablative electrode has cutouts defined therein and the orthogonal electrodes as disposed in the catheter within the cutouts.

Alternatively, the orthogonal electrodes are disposed on the catheter and extend through the cutouts. The catheter further comprises insulated mesas disposed over the cutouts and the orthogonal electrodes are disposed on the mesas.

Thus, the invention can be defined as a catheter for ablating myocardium in a human heart in a heart comprising a catheter body for disposition within the heart. At least one pair of orthogonal electrodes is disposed on the catheter body for sensing localized cardiac activity only in myocardium within 1 to 3 mm adjacent to a predetermined point within the myocardium. A circuit is coupled to the pair of orthogonal electrodes and differences the cardiac signals sensed by the at least one pair of orthogonal electrodes to generate an electrographic signal indicative only of localized cardiac activity only within 1 to 3 mm of the predetermined point in the myocardium. An ablative electrode is disposed on the catheter for applying energy through the ablative electrode to extirpate myocardium in contact with the ablative electrode. The orthogonal electrodes are disposed within the ablative electrode. The orthogonal electrodes and circuit for differencing cardiac signals are arranged and adapted for simultaneously sensing only the localized cardiac activity of the myocardium at the predetermined point while the myocardium in contact with the ablative electrode is extirpated. As a result, the catheter is provided for ablating selected myocardium in the heart in response only to localized cardiac signals from myocardium at a specific spatial point. The closest of the orthogonal electrodes are disposed within 1 to 5 millimeters from the ablative electrode.

The invention is also defined as a method for ablating myocardium of a heart comprising the steps of disposing a catheter within the heart at a position adjacent to a predetermined point in the myocardium. Only localized cardiac signals from the myocardium within about 1 to 3 mm adjacent to the predetermined point are sensed without necessarily contacting the myocardium. Energy is applied through the catheter at the predetermined point for the purpose of ablating myocardium at the predetermined point.

The steps of sensing and ablating may be simultaneous or sequential. The step of applying energy is performed by applying radio frequency ablative energy through an ablative tip at a distal end of the catheter.

The invention may be better visualized by now turning to the follow drawing wherein like elements are referenced by like numerals.

The invention and its various embodiments may now be better understood by turning to the following detailed description.

DETAILED DESCRIPTION OF THE PREFERRED EMBODIMENTS

Orthogonal sensors, which are comprised of two or more electrodes and generally disposed circumferentially on the catheter at given longitudinal point along the catheter, receive signals which are differenced within a differential amplifier to produce a signal indicative only of the localized biopotential heart activity at a predetermined point in the myocardium. The orthogonal sensors are disposed in an ablative tip of the catheter to allow sensing of the localized cardiac activity which is adjacent to or in contact with the ablative tip during extirpation procedure or during the delivery of radio frequency energy during ablation. Sensing of the localized cardiac activity occurs simultaneously either with the ablation so that detailed and accurate electrocardiograms of the very tissue being ablated can be recorded.

Figure 1:
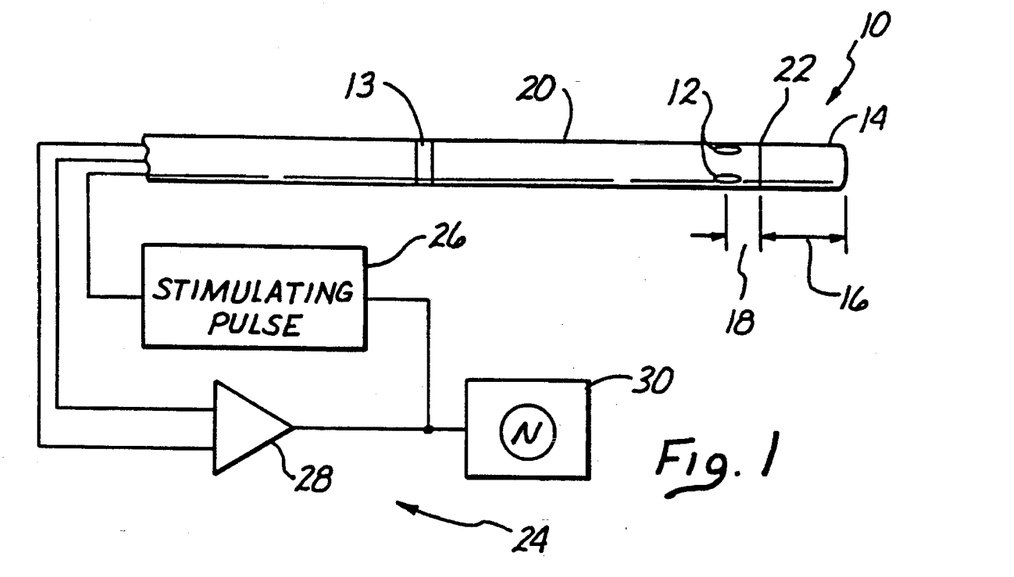
FIG. 1 is a diagrammatic depiction of a catheter employed according to the invention in which a single set of orthogonal electrodes are used.

FIG. 1 is a diagrammatic depiction of a catheter 10 incorporating a plurality of orthogonal sensing electrodes 12. Sensing electrodes 12 are disposed on catheter 10 behind a stimulating tip 14. In the embodiment of FIG. 1, tip 14 has a length 16 of approximately 2 to 4 millimeters. Any structure of stimulating tip 14 now known or later devised for ablation, pacing or other applications where energy or signals are transferred to myocardial may be used and are expressly contemplated as being within the scope of the invention.

Electrodes 12 are positioned in or on catheter body 20 at a distance 18 of approximately 1 to 3 millimeters behind or above the rearmost edge 22 of tip 14. Tip 14 and electrodes 12 are coupled to wires within catheter 10 and ultimately led to circuitry 24. The detail and nature of circuitry 24 is largely immaterial to the invention and therefore will not be further described other than to state that tip 14 is driven by a circuit 26 for generating a stimulating or ablating pulse and that sensing electrodes 12 are coupled in a pairwise fashion to one or more differential amplifiers 28 for generating a difference signal between selected one of the electrodes. The difference signal is provided as an input to pulse generator 26 or to a monitor 30 to generate a time trace of the differential signal across two or more of the sensing electrodes 12. The difference signal may be subject to additional signal processing in conventional circuitry not explicitly depicted, such as signal conditioning or logical processing to develop the signal which is ultimately displayed in monitor 30 or used in pulse generator 26.

In the simplified embodiment of FIG. 1, only two orthogonal sensing electrodes 12 are shown although it is expressly contemplated that any number may be disposed within body 20 of catheter 10. For example, three such electrodes 12 may be disposed equal distantly around the circumference of body 20 of catheter 10 to provide from two to three differential signals for cardiac mapping.

It is also contemplated that monitor 30 may include a computer which will further process multiple signals from the plurality of differential amplifiers to generate various averages of the differential signals or other conventional statistical measures which will be indicative of the local electrical signals from the myocardial tissue proximate to sensing electrodes 12.

Still further, although sensing electrodes 12 have been shown in FIG. 1 to be disposed within a single circumferential, cylindrical band in body 20, it is also expressly contemplated that the electrodes may be displaced in a staggered fashion, that is one electrode placed further from edge 22 than another in order to provide both a different electrode pattern in space, but also to provide greater physical space on electrode 20 for the disposition of larger sensing electrodes. A ring electrode 13 may also be provided and used as part of a bipolar pacing array.

In this respect, whether electrodes 12 are insulated from contact with the blood, are provided with articulated surfaces for increasing the surface area available for blood contact without increasing the overall geometry of the sensing electrode, or otherwise incorporate various electrical improvements for coupling to circuitry 24 or for electrophysiological coupling is secondary to the invention which contemplates using any type orthogonal sensors now known or later devised, which are closely enough positioned with respect to stimulating tip 14 to provide an orthogonal electrogram of the myocardial activity in the proximity of tip 14. This is clearly advantageous where catheter 10 is used for local extirpation or ablation. A reliable identification of the abnormal myocardial site must be made in the proximity of the device which is used to obliterate or otherwise remove the abnormal tissue. In this sense, it is expressly contemplated that stimulating tip 14 may be replaced by any number of other different types of devices for extirpation or ablation to effect the removal or obliteration of the abnormal myocardium.

Figure 2:
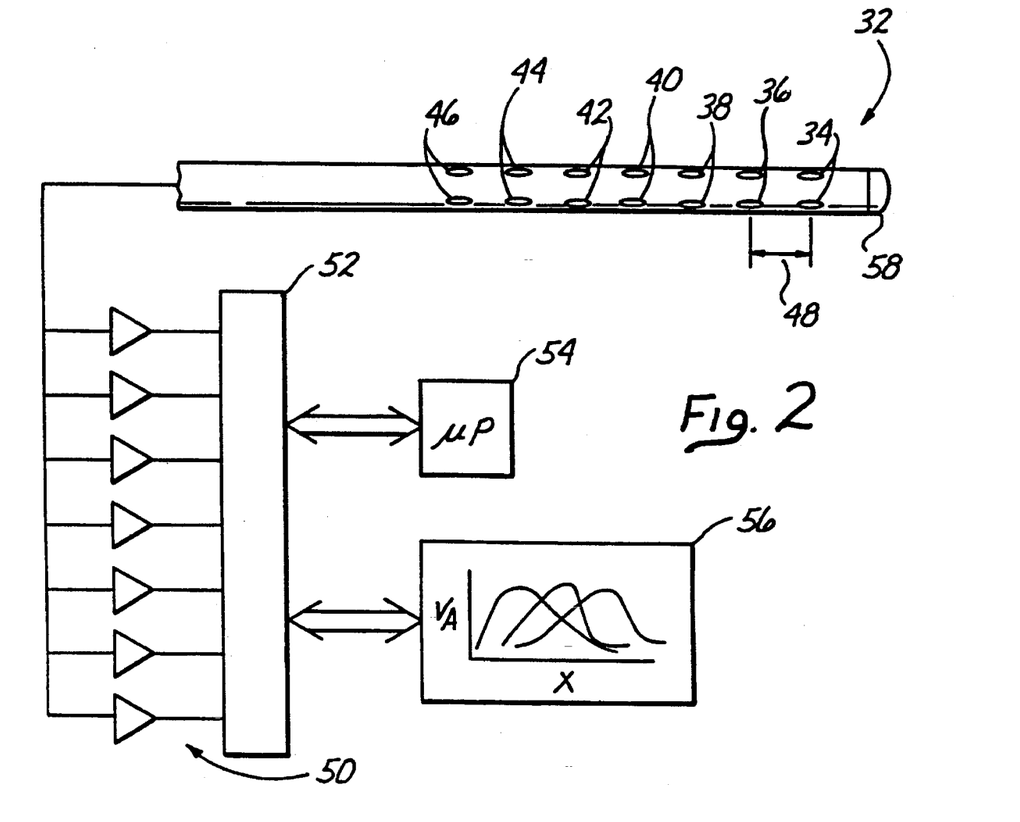
FIG. 2 is a diagrammatic depiction of a catheter employed according to the invention in which multiple sets of orthogonal electrodes are used.

FIG. 2 is a simplified depiction of another embodiment of the invention wherein a sensing catheter 32 is employed with a plurality of sets of orthogonal electrodes 34–46. In the illustrated embodiment of FIG. 2, each set is illustrated as being comprised of at least two electrodes and seven such sets are shown along the longitudinal length of catheter 32, although both the number of electrodes within each set as well as the number of sets on catheter 32 can be varied according to the application. Each set of electrodes 34–46 is separated from the adjacent set of electrodes 34–46 by a distance 48 of approximately 3 to 5 millimeters. Catheter 32 is a stearable cardiac catheter which can be used for activation mapping within the heart. Catheter 32 is laid against the atrial or ventricle walls or at least in the near proximity to them to monitor the direction of electrical activation. Direct contact with the myocardial tissue is not necessary. Signals from sets of electrodes 34–46 may be each individually coupled to the separate wire or multiplexed on a bus for input to a corresponding plurality of differential amplifiers 50. The output of amplifiers 50 are then provided after appropriate signal conditioning to digital bus 52 and computer 54 to provide an oscillographic or graphic map of the activation voltage by conventional output device 56, such as an oscilloscope or plotter. Again, the electronics which may be used in combination with the catheter of the embodiment of FIG. 2 is largely inconsequential and is suggested here only for the sake of completeness.

It has been determined that by use of a catheter having four pairs of orthogonal electrodes spaced at 5 millimeters apart in a configuration similar to that shown in FIG. 2 that differences of 16 milliseconds in the right atrium of the human heart can be easily recorded between sets of sensing orthogonal electrodes located only two centimeters apart and positioned along the lateral atrial wall. Therefore, a catheter of the type illustrated has particular utility for use in clinical electrophysiology for localizing a site within the heart from which abnormal rhythms originate. Catheter 32 is used to map the heart and to identify the area within the heart in which the endocardial surface activation in the heart most nearly identically matches that of a spontaneous arrhythmia either of a predetermined type or of a type actually measured from the patient during the arrhythmia from both the catheter electrodes and from normal skin contact EKG. Such mapping and matching in three dimensions to a model of a patient's heart can be automated through computer 54 as contemplated in the context of the embodiment of FIG. 2.

Catheter 32 may also be provided with a stimulating tip 58 so that the heart can be stimulated during the mapping process to test heart functions or arrhythmias while the activation sequence of the near field heart potential is simultaneously sensed by each of the plurality of sets of orthogonal electrodes 34–46. Simultaneous sensing while pacing or stimulating cannot be performed with conventional tip to ring electrodes which have a substantial signal pickup from the stimulating pulse. Simultaneous recording of localized electrograms can be accomplished in the present invention with either the single set of orthogonal electrodes 12 shown in FIG. 1 or with a array of such sets as shown in the embodiment of FIG. 2.

Figure 5:
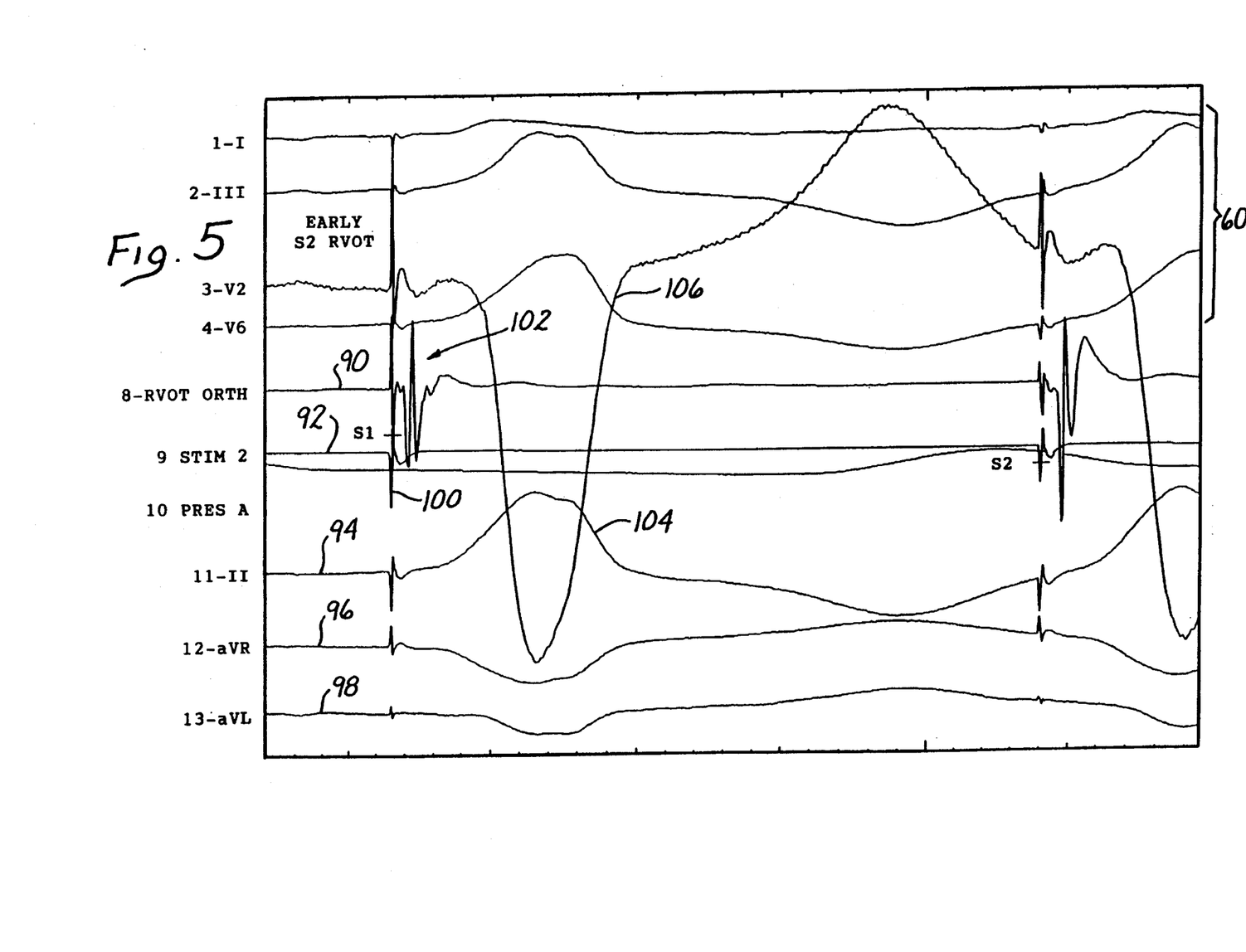
FIG. 5 is an actual human electrocardiogram produced according to the invention which illustrates specific sensing of tissue being stimulated by pacing in the right ventricular outflow track.
Figure 6:
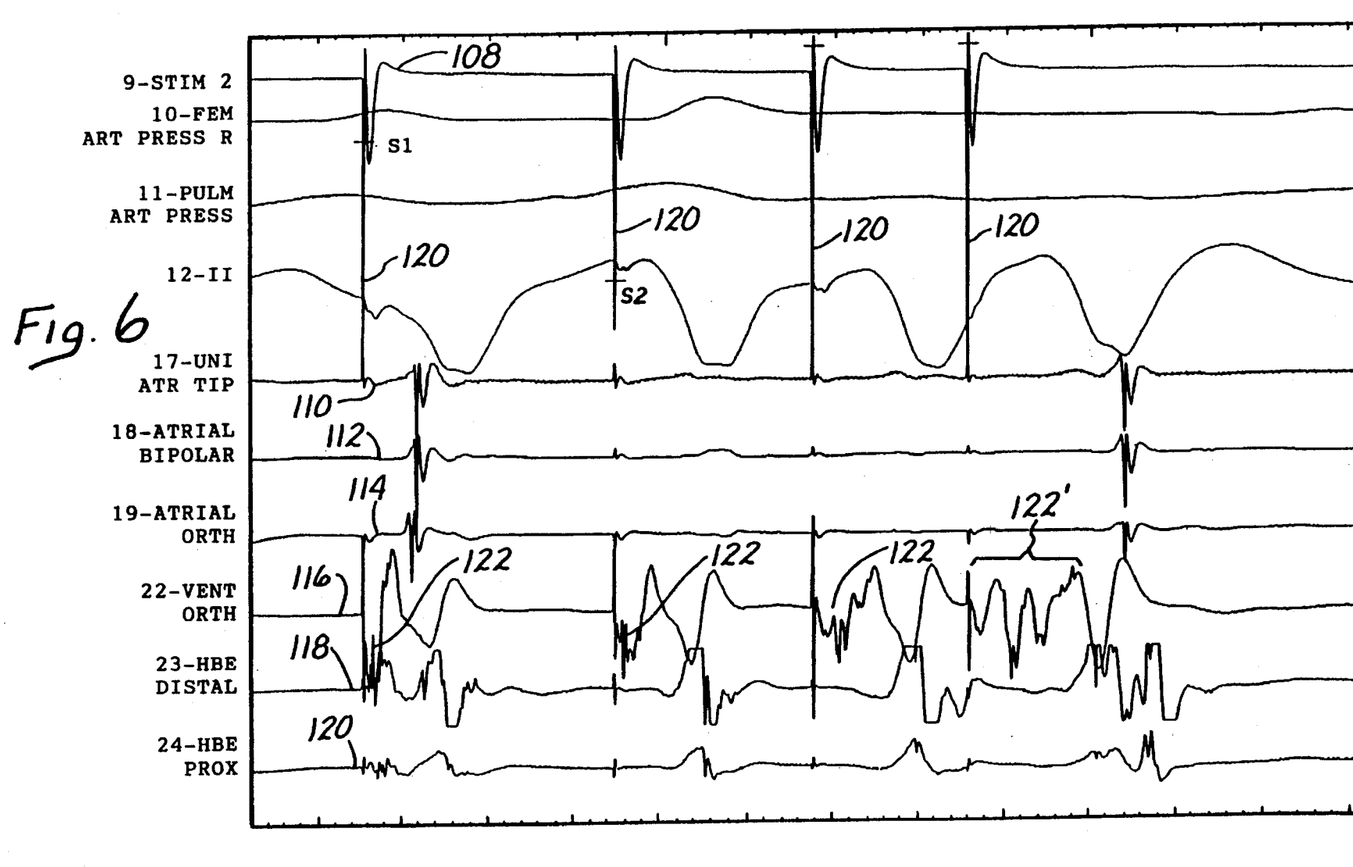
FIG. 6 is an actual human electrocardiogram produced according to the invention which illustrates specific sensing of tissue which is simultaneously being stimulated by pacing and which stimulated tissue is subject to localized fragmentation of electrical activation and therefore ventricular tachycardia.

Recent investigations have revealed that intracardiac sensing according to the invention is so discrete that stimulation during the relative refractory period of the tissue will still detect a localized near potential of the tissue which is generated even prior to activation as seen on a surface EKG (FIGS. 5 and 6). As the stimulus is applied at earlier times during the period of tissue refractoriness, as shown in FIG. 6, the orthogonal electrogram sensed by probes of the invention shows a cardiac response which becomes more and more fragmented with a delay showing of the slow speed of excitation in the localized muscle being stimulated. Therefore, the use of the sensing probes of the invention in pace mapping to find the sites within the heart of abnormal heart rhythms is particularly advantageous since reliable identification of such abnormal sites is based on upon being able to identify those areas of slow excitation responsible for reentry. Using orthogonal electrodes immediately behind a stimulating tip, the identified areas of slow excitation can be easily discriminated from areas of normal activation. This identification can then be exploited in subsequent steps of local extirpation or ablation.

The use of radio frequency localized diathermy for purposes of cardiac ablation is increasingly being used on abnormal heart muscle responsible for abnormal heart rhythms. Conventional catheter designs cannot record the myocardial activity of the ablated area during the ablation period. With orthogonal electrodes spaced at 1–3 mm proximal to the ablating tip according to the invention, energy can be applied to and cardiac recordings made of the local myocardial tissue as it is being subject to ablation. This allows direct observations to be made of localized signals and allows the physician to judge the efficiency of the ablation procedure in destroying the abnormal tissue.

It has been demonstrated by the invention that sensing from the electrode array on the catheter is so discrete, that stimulation during the relative refractory period of the adjacent tissue shows localized near potentials which occur even prior to the activation as seen on the surface. As stimuli occur earlier and earlier during the tissue refractoriness, the orthogonal electrogram becomes more and more fragmented and delayed showing the slow spread of excitation in the localized muscle. This finding is important since pace mapping to find the site of abnormal heart rhythms relies on finding the area of slow excitation responsible for reentry. Using orthogonal electrodes immediately behind the stimulating tip, the area of slow versus normal activation can be discriminated for the proposes of local extirpation or ablation.

Figure 3:
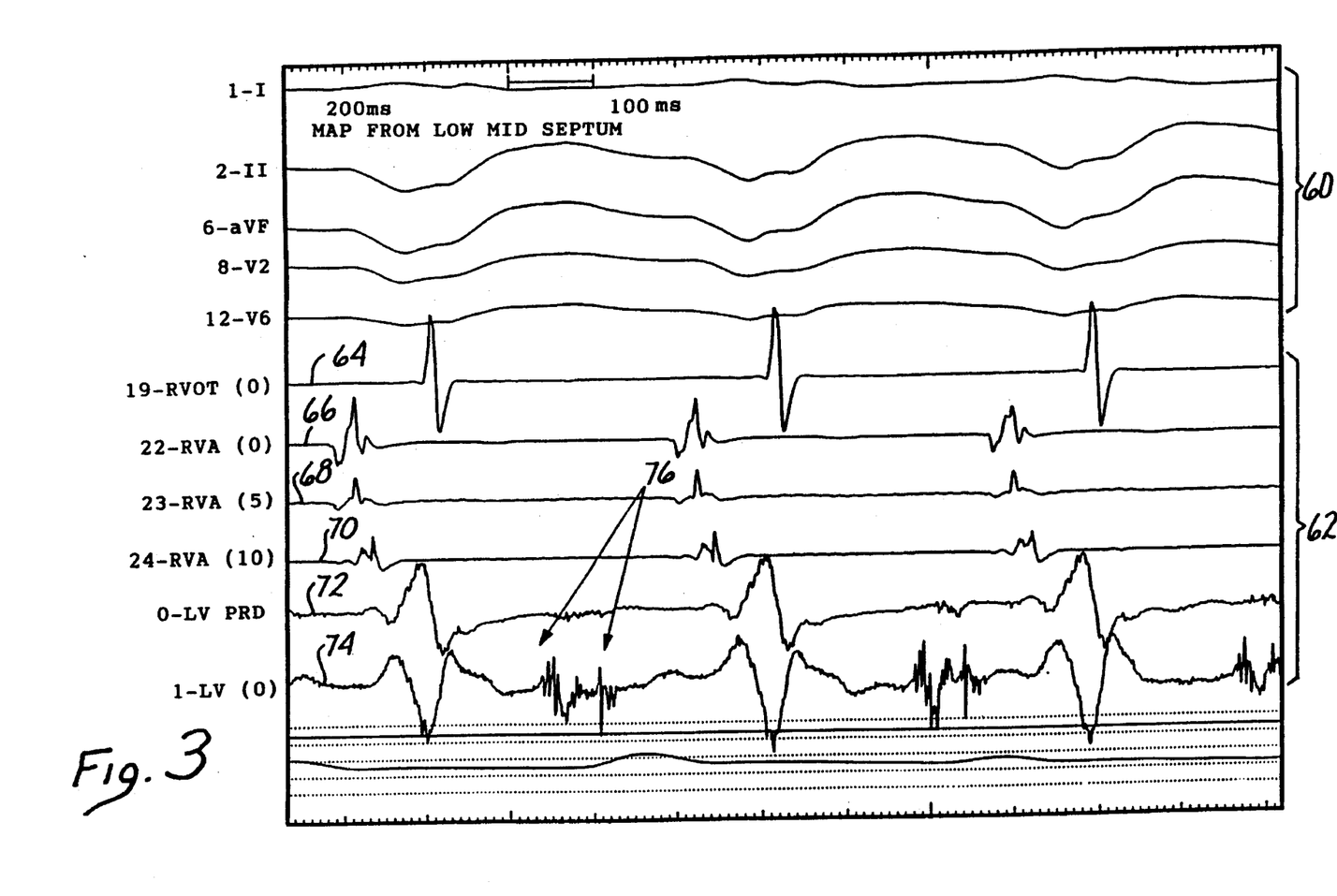
FIG. 3 is an actual human electrocardiogram produced according to the invention which illustrates tissue specific intracardiac mapping of an abnormal heart rhythm from a specific heart site.

The disclosed catheter and its method of use is graphically illustrated in the human electrocardiograms depicted in FIGS. 3–9. FIG. 3 is an actual human electrocardiogram in which the upper five lines represent the time trace of a conventional surface electrocardiogram. Trace 64 is obtained from a catheter similar to that described in FIG. 1 wherein the orthogonal electrodes immediately behind the stimulating tip are placed in the in the right ventricular outflow track. Traces 62 are the signals sensed at three separate orthogonal electrode locations longitudinally disposed along the length of the catheter similar to that described in FIG. 2 whose tip is placed in the right ventricular apex. Traces 66–70 are in the right ventricular apex (RVA) at distances of 5 mm separation. Traces 72 and 74 are obtained from a catheter such as in FIG. 1 which has been positioned in the left ventricle during an episode of a sustained abnormal heart rhythm, ventricular tachycardia. Trace 72 is a standard bipolar electrogram recorded between the tip and ring of the mapping catheter. Trace 74 is the orthogonal electrogram obtained from a pair of orthogonal electrodes disposed 1 mm behind the distal stimulating tip. The tip of the catheter in the left ventricle has been positioned near the low mid interventricular septum.

Each of the orthogonal electrodes in the catheter used to make traces 66–70 of FIG. 3 were evenly spaced from each other along the length of the catheter starting from the tip at approximately 5 millimeters apart. This catheter was positioned in the right ventricular apex and along with the two other orthogonal catheters positioned in the right ventricular outflow tract and left ventricle to determine the timing of local endocardial activation and thus the direction of spread of electrical activity during this abnormal heart rhythm. Physical contact between the orthogonal electrodes and the heart walls is not necessary in order for the catheters to function in reflecting localized endocardial activation. As can be seen in FIG. 3, RVOT activation is very late in comparison to the RVA recordings. Furthermore, activation in the RVA proceeds from the most distal to the most proximal orthogonal electrode.

The tracing obtained from the catheter positioned in the left ventricle however, are most revealing. For example, the pattern denoted by reference numeral 76 in FIG. 3 shows an irregular and fragmented local cardiac activity occurring extremely early in comparison to all other areas of myocardium from which signals are recorded. This fragmented activity is barely discernible from the standard tip to ring recording configuration (trace 72). Orthogonal electrodes because of their unique sensing properties show this fragmented activity which indicates that this area is that responsible for the sustained arrhythmia. The local activity reflecting a site of early slow conduction is responsible for this ventricular tachycardia and occurs only in the specific position corresponding to the electrode receiving trace 74 and does not appear on the electrode recordings made at any other intracardiac site.

Thus, the electrograms depicted in FIG. 3 dramatically and graphically illustrates the spatial specificity of the methodology and structure of the catheters to allow pinpoint identification of internal cardiac sites from which arrhythmias arise.

Figure 4:
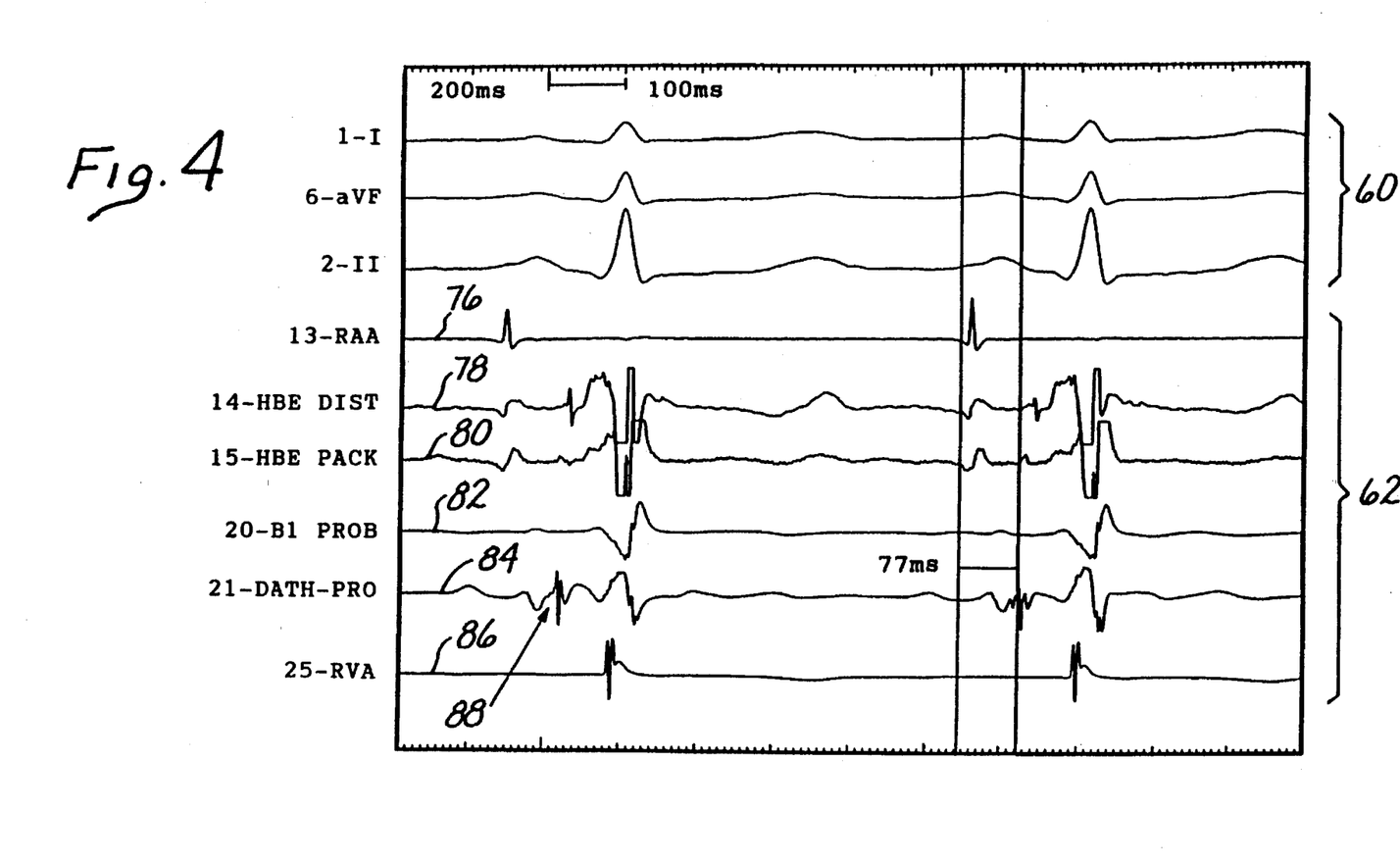
FIG. 4 is an actual human electrocardiogram produced according to the invention which illustrates tissue specific mapping of a slow pathway potential at a specific heart site.

FIG. 4 is an actual human electrocardiogram of another subject obtained using the catheter described above and shown in FIG. 1. Again, a conventional surface electrocardiogram is shown by traces 60 with the traces 76–86 taken from various intracardiac electrodes. Tracings 82 and 84 are taken from the catheter shown in FIG. 1 positioned inferior and posterior along the annulus fibrosus of the tricuspid valve inside the right heart. Pattern 88 on trace 84 illustrates a a very large amplitude slow pathway potential recorded from orthogonal electrodes and not seen in simultaneously recorded trace 82 derived from the tip-ring bipole of this same catheter. The area from which slow pathway potentials are recorded occurring during a normal sinus rhythm is the precise area utilized for AV nodal reentry responsible for paroxysmal supraventricular tachycardia. Pattern 88 is regarded as a slow pathway potential because of its timing and discreteness characteristics amplified by orthogonal recordings immediately behind the stimulating tip. When ablative RF energy was applied to this area via the stimulating tip, the slow pathway was ablated and the patients arrhythmia cured.

FIG. 4 is, thus, a dramatic illustration of the spatial specificity of the methodology of the invention. That electrode responsible for trace 84 monitors specifically adjacent heart tissue in which the slow pathway pattern 88 can be identified and yet the same pattern does not appear on electrodes responsible for trace 82.

FIG. 5 is an actual human electrocardiogram of a subject, again, in which the upper four traces are conventional surface electrocardiogram 60. Trace 90 is the orthogonal electrogram derived from electrodes immediately proximal to the stimulating of a catheter of FIG. 1 design, which has been placed in the right ventricular outflow tract (RVOT). Trace 92 is the trace corresponding to a marker for the pacing pulse delivered through the tip of the catheter. The stimulating pulse illustrated by waveform 100 produces a localized response never before observed and indicated by waveform 102. Waveform 102 occurs in advance of the propagated response of the heart tissue seen later within the myocardium on surface leads trace 94 as pattern 104 and in the other surface electrocardiograms 60 as pattern 106. Therefore, FIG. 5 is a graphic illustration of how the catheter of the invention and methodology of its use can show an extremely local response reflecting activation of the actual tissue being stimulated before a propagated response from that very tissue is seen.

FIG. 6 is an actual human electrocardiogram from another patient subject to pacing showing a surface electrocardiogram reflected in trace 60 and a stimulating pulse shown on trace 108. The remaining traces 110–120 are signals taken from various intracardiac electrodes. Traces 110–114 are recorded from the right atrial appendage. Trace 116 is a signal received on the orthogonal electrode pair positioned in the right ventricular apex of the heart and immediately proximal to the stimulating tip used for ventricular pacing. What is seen for the first time is a spatially specific localized electrophysiologic activity indicative of the type of slow fragmented myocardial activation responsible for arrhythmias such as ventricular tachycardia. The pacing spikes 120 are shown as being delivered to the catheter tip at shorter and shorter time intervals. The sensed and stimulated location within the heart is indicated on trace 116, approximately 1 millimeter away from catheter tip. Trace 116 shows a series of premature beats in response to pacing stimuli which occur at times when the paced tissue is increasingly refractory. What is seen for the first time are patterns 122 occurring prior to propagation of the stimulated beat at the sensed location. As the local tissue becomes increasingly refractory to stimulation, the local near field electrograms recorded from the stimulated tissue show increasingly chaotic and fragmented responses as depicted by progressive prolongation in the duration of pattern 122. Therefore FIG. 6 is a clear demonstration of the ability of the present invention to clearly identify local responsive electrophysiologic activities at specific heart sites simultaneously to the heart is being paced from that precise site.

Figure 7:
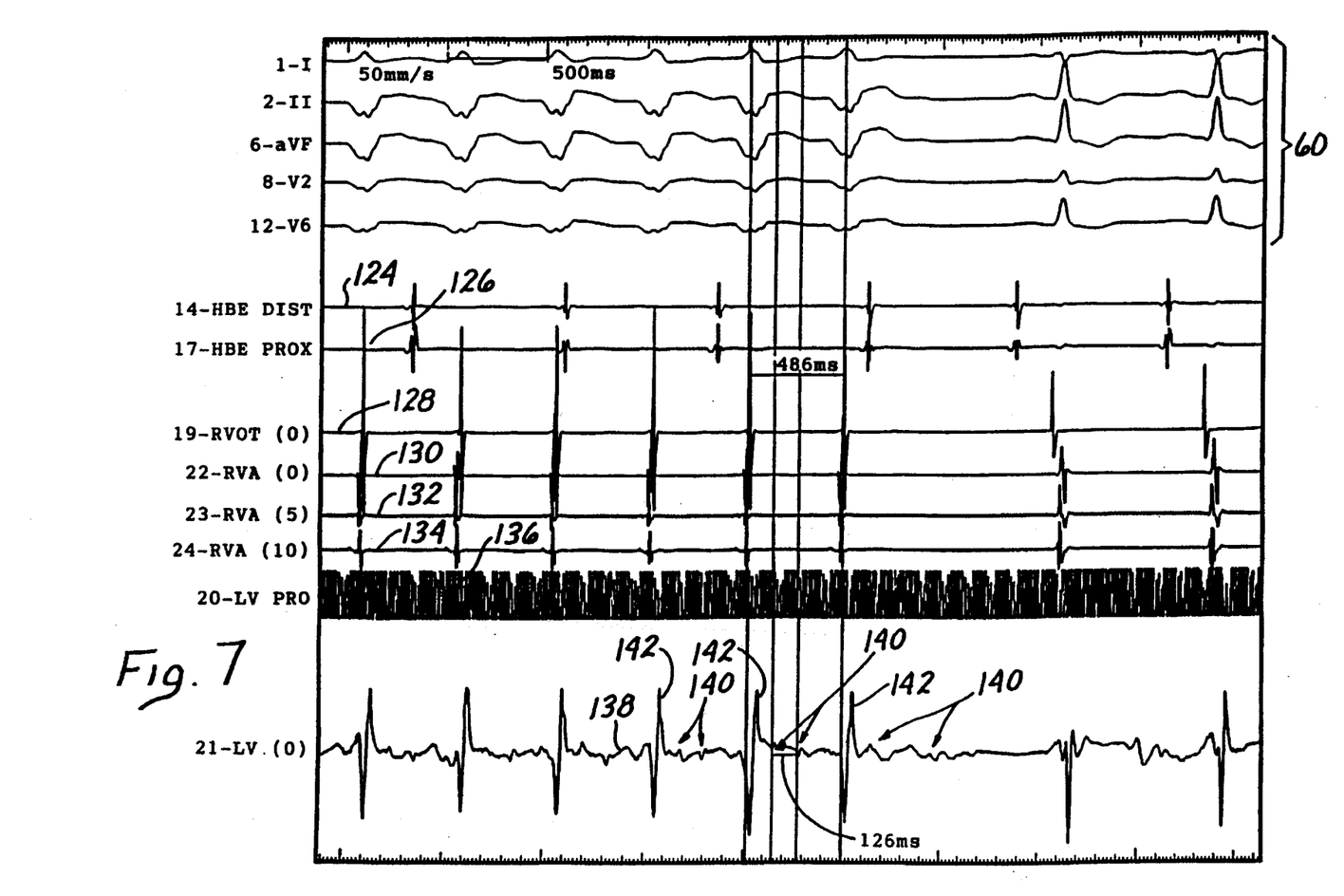
FIG. 7 is an actual human electrocardiogram produced according to the invention which illustrates specific sensing of tissue which is simultaneously being ablated by an RF signal wherein the process of extirpation over time of a specific tissue site is being shown.

FIG. 7 is an actual human electrocardiogram, again, having a normal surface electrogram 60. His bundle electrograms recorded by standard means are showing traces 124 and 126. Orthogonal electrode signals are shown in traces 128–134 and 138, and with an RF ablation signal shown in trace 136. The electrodes which produced the clear heart trace on trace 138 are positioned approximately 1 millimeter from the ablating tip on a catheter similar to that depicted in FIG. 1. FIG. 7 demonstrates that the invention is capable of clearly delineating localized heart activity while ablation is simultaneously occurring not only in the heart but from the tissue actually subject to the ablative energy. FIG. 7 illustrates the RF ablation occurring during an episode of ventricular tachycardia where the destruction of localized tissue results in cure of the arrhythmia. The electrode from whence the trace 138 is taken is sensing the very tissue being ablated and shows fragmentation of the electrocardiogram patterns 140. The regular propagating wave form of the ventricular tachycardia is shown by pattern 142. As the myocardium responsible for this ventricular is destroyed by RF energy, waveform 140 shows progressive fragmentation and conduction delay indicative of tissue ablation. When conduction delay is extended to nearly 350 msec the arrhythmia terminates and was in fact no longer inducible.

The abnormal tissue, thus, giving rise to the ventricular tachycardia is not only accurately spatially identified prior to the application of RF energy, but in addition, during the ablation the amount of alteration of conduction and the efficacy of the ablative energy is simultaneously monitored In addition, if for any reason the ablation is ineffective to remove the electrophysiological cardiac aberration, the procedure can be terminated early, before unnecessary cardiac tissue extirpation occurs. The phenomena depicted in FIG. 7 have never been recorded in a human heart prior to the present application of the described technology.

Figure 8:
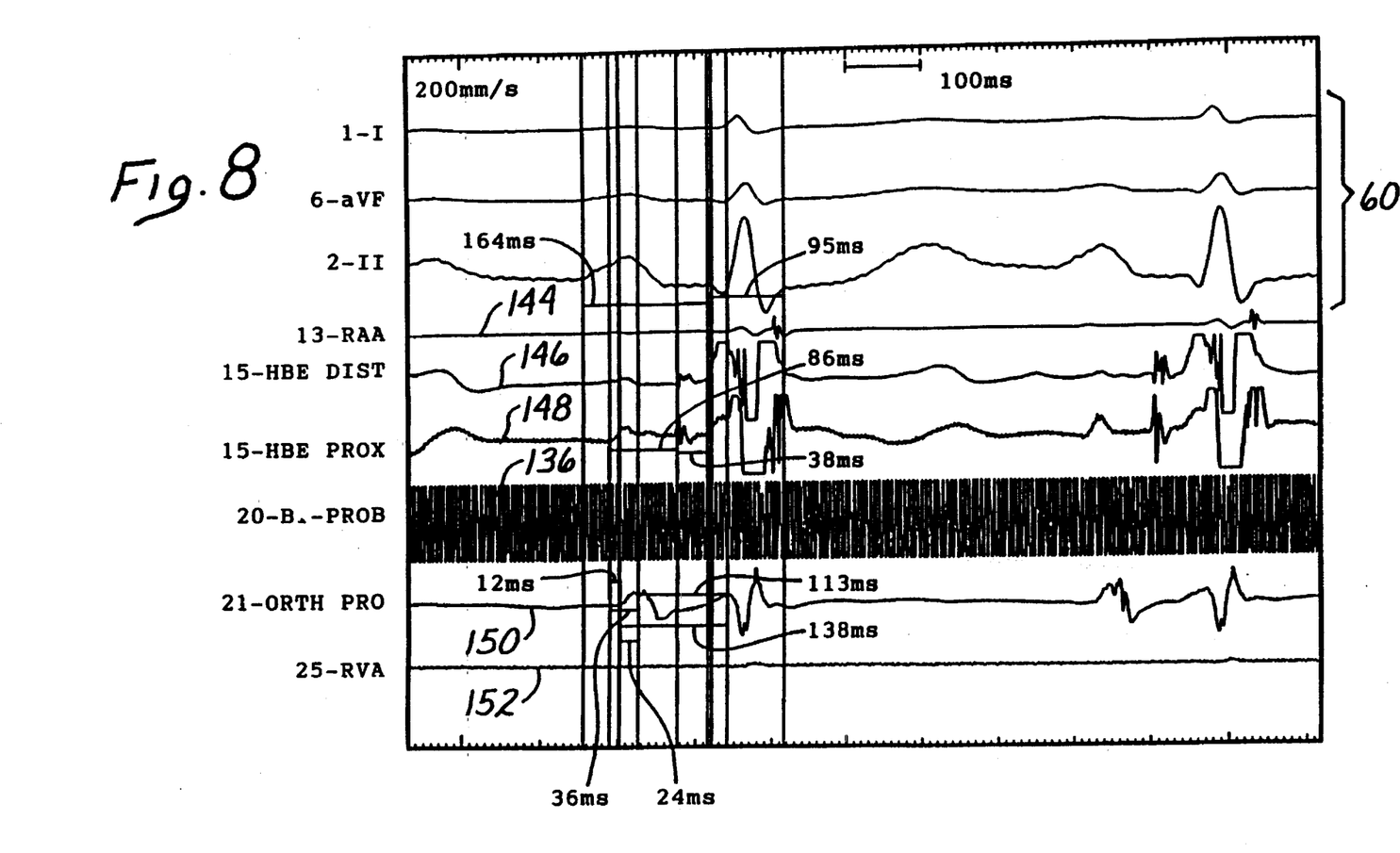
FIG. 8 is an actual human electrocardiogram produced according to the invention which illustrates specific sensing of tissue which is simultaneously being ablated by an RF signal wherein discrete electrograms of a specific tissue site is being shown as the tissue is being ablated.

FIG. 8 is an actual human electrocardiogram obtained during an ablation for paroxysmal reentrant supraventricular tachycardia. Similar to that shown in FIG. 7, wherein the heart electrophysiologic activity received by the electrode producing trace 150, are orthogonal electrodes located 1 mm proximal to the tip electrodes. Trace 150 is an electrogram derived from the slow pathway area of conduction recorded from the tissue being ablated. The tracing again clearly demonstrates the ability to show discrete electrograms in any heart site while the high intensity, high frequency RF ablation energy is simultaneously being delivered to the ablation site.

Figure 9:
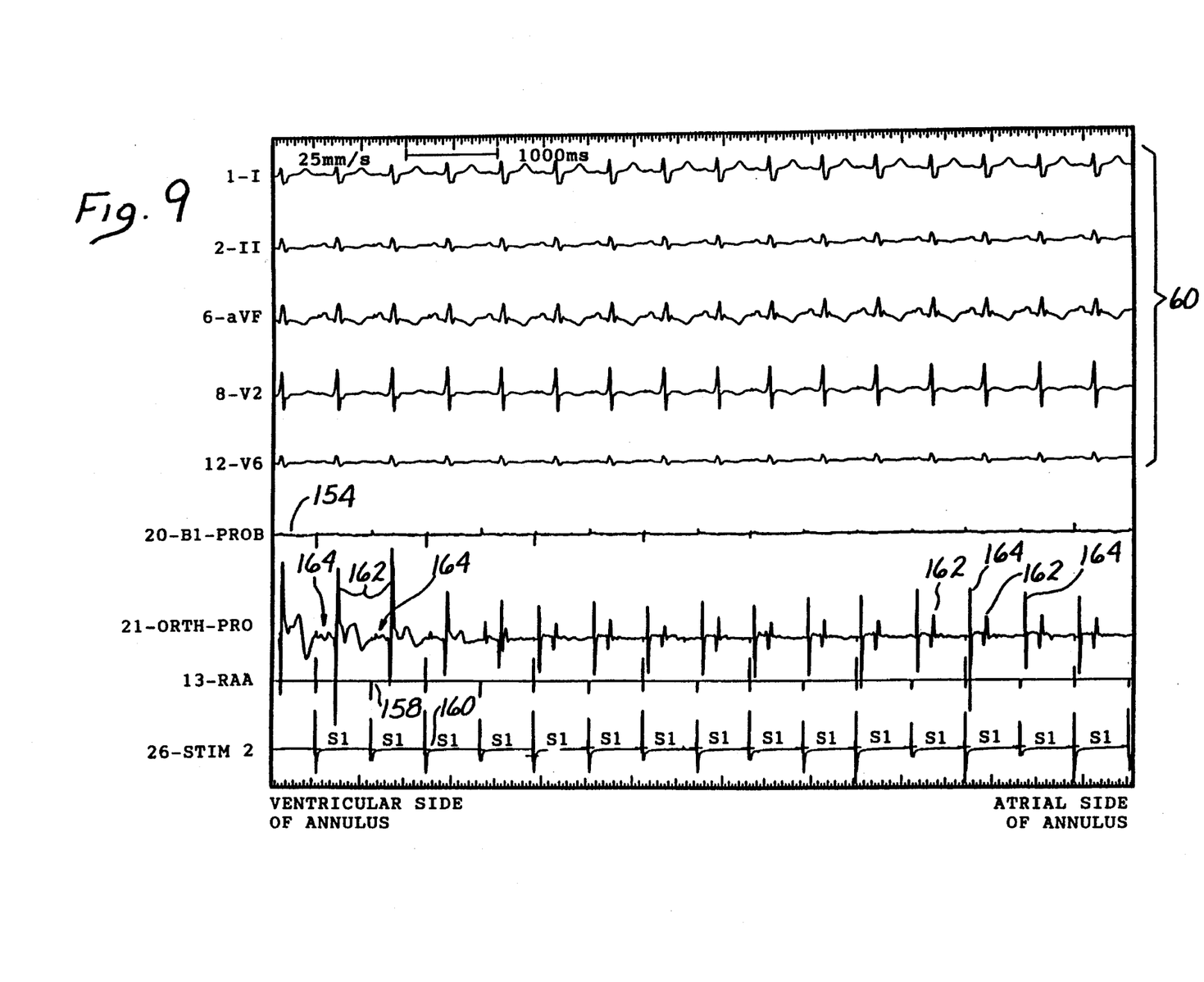
FIG. 9 is an actual human electrocardiogram produced according to the invention which illustrates specific mapping of tissue as the catheter is moved from ventricular to the atrial side of the right heart annulus.

FIG. 9 is yet another actual human electrocardiogram taken during an ablation procedure (the RF ablation signal has been omitted for the sake of clarity), which further demonstrates the spatial specific characteristics of the invention. Here an orthogonal electrode immediately proximal to the electrode tip produces a trace 156. During the recording the catheter inadvertently moved from the ventricular side of the annulus of the valve between the atrium and ventricle to the atrial side. On trace 156, it can be demonstrated on the left hand side of FIG. 9 the pattern is dominated by large ventricular spikes 162 and the smaller atrial pulses 164. As the electrode responsible for trace 156 moved through the valve annulus to the atrial side, the pattern progressively changes such that the large ventricular signals 162 become smaller and the atrial signals 164 become more prominent, eventually exceeding those of the right ventricle.

This type of pattern recognition would, for example, become very important when electrophysiological procedures were being undertaken with respect to tissue in the vicinity of the heart valve, like ablation. Movement represented in FIG. 9 is probably less than 5 millimeters and was not detectable with standard fluoroscopic means. This type of catheter movement probably frequently occurs under normal circumstances in a beating heart with a catheter disposed almost anywhere within it and more particularly adjacent to an opening and closing valve. It is essential during RF ablation however to know whether the catheter tip is actually on the ventricular or atrial side of that valve annulus. Only the present methodology allows for that discriminate a signal such that this could be recognized during RF ablation.

Figure 10:
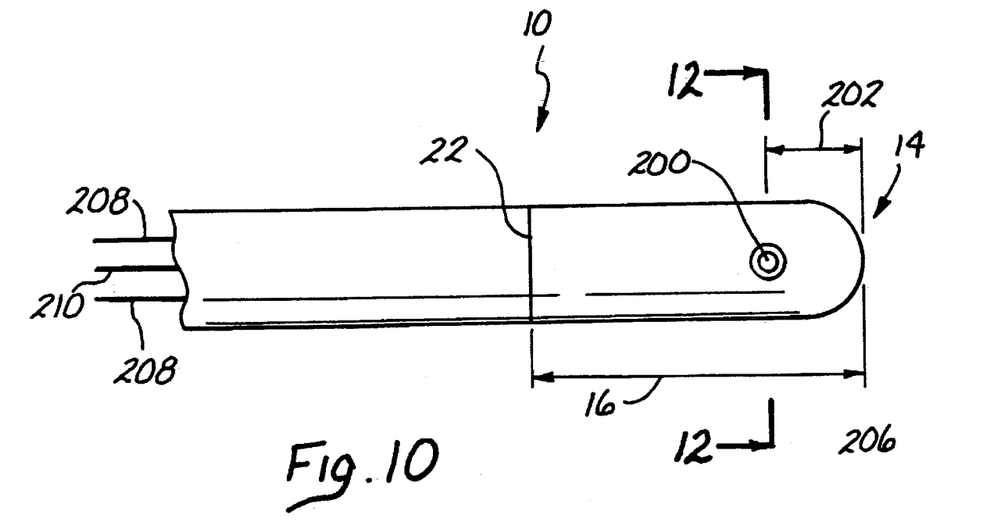
FIG. 10 is an enlarged side view of the end portion of a catheter of the invention wherein the sensing electrodes are disposed in cutouts defined in the ablative tip itself.

FIG. 10 illustrates another embodiment of catheter 10 wherein ablation tip 14 is enlarged from 2–4 mm in length 16 in the embodiment of FIG. 1 to a much larger and longer tip. For example, tip 14 is contemplated as being lengthened to 6–12 mm in length or longer. As ablating tip 14 increases in length and hence area, the ability to use tip 14 itself as a sensing electrode dramatically decreases. Increasing the size of tip 14 may be motivated for a number of reasons including better tuning for ablating frequencies or better radio frequency gains. Therefore, orthogonal sensing electrodes will not be placeable near the distal end of tip 14 and may be as far distant as 6 to 12 mm away. This will in effect prevent the sensing of the ablated tissue.

To solve this problem, the embodiment of FIG. 10 includes orthogonal sensing electrodes 200 which are electrically isolated from ablation tip 14, but placed within a small predetermined distance 202 of the distal end of tip 14. In the illustrated embodiment electrodes 200 are disposed within 1 mm of the distal end of tip 14. Two or more electrodes 200 may be utilized as orthogonal electrodes consistent with the teaching of this invention and may be fabricated in tip 14 and disposed on the end of catheter 10 within cutouts 204 defined through the conductive element which comprises ablative tip 14 as shown in cross section in FIG. 11. Leads 208 are coupled to electrodes 200 and couple the electrodes as described above to differential amplifier 28. Ablative electrode tip 14 is coupled to lead 210 through which the ablative energy is delivered from a signal source 26. Leads 208 and 210 are appropriately shielded and insulated from each other in catheter 10 to avoid inadvertent interconnection and crosstalk.

Figure 11:
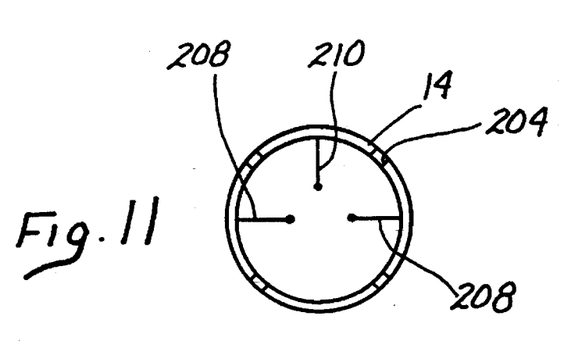
FIG. 11 is a cross-sectional view of FIG. 10 taken through section lines S—S where the sensing electrodes are disposed in the cutouts.
Figure 12:
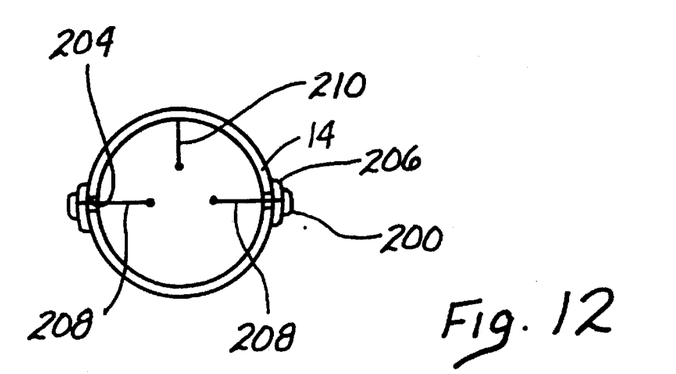
FIG. 12 is a cross-sectional view of FIG. 10 taken through section lines S—S where the sensing electrodes are disposed through the cutouts and on top of insulating mesas disposed over the cutouts and on the ablative tip.

If desired electrodes 200 may be enlarged to a size greater than the size of cutouts 204, and disposed on an insulating mesa 206 over and on the outside of ablative tip 14 as shown in cross section in FIG. 12. A single pair of electrodes 200 are illustrated in FIGS. 10–12, but it is expressly contemplated that more pairs may be employed at different distances from the distal end of tip 14 and/or at different azimuthal orientations on tip 14, or that odd numbers of electrodes forming pairs with shared electrodes can be used in any geometric combination desired. Also no limitation is to be read on the nature of the electrodes themselves, which may be made of different materials, with different structures and shapes. For example, electrodes 200 may made of noble metal, semiconductive or resistive materials and fabricated as solid, screen, or complexly surface textured electrodes in the shape of circles, triangles, squares or complex topological shapes.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An ablating catheter for ablation of myocardium in a human heart comprising:

a catheter body for disposition within said heart, said catheter body having a distal tip;

an ablative electrode disposed on said distal tip;

at least one pair of orthogonal electrodes disposed in said ablative electrode and electrically insulated therefrom for receiving electrocardiac signals only from a localized area within said myocardium, which area is ablated; and circuit means for differencing cardiac signals received by said at least one pair of orthogonal electrodes to generate an electrographic signal indicative of localized cardiac activity at said area, whereby said catheter is usable for ablating and sensing electrophysiologic activity of said ablated myocardium without substantial alteration of the size of said ablative electrode.

2. The catheter of claim 1 wherein said orthogonal electrodes simultaneously sense electrophysiologic activity at a predetermined point in said myocardium being ablated.

3. The catheter of claim 1 wherein said orthogonal electrodes are disposed in said ablative electrode within 1 to 5 millimeters from said distal tip.

4. The catheter of claim 1 wherein said ablative electrode has cutouts defined therein and wherein said orthogonal electrodes are disposed in said catheter within said cutouts.

5. The catheter of claim 1 wherein said ablative electrode has cutouts defined therein and wherein said orthogonal electrodes are disposed on said catheter and extend through said cutouts.

6. The catheter of claim 5 further comprising insulated means disposed over said cutouts and wherein said orthogonal electrodes are disposed on said means.

7. A catheter for ablating myocardium in a heart comprising:

a catheter body for disposition within said heart;

at least one pair of orthogonal electrodes disposed on said catheter body for sensing localized cardiac activity only in myocardium within 1 to 3 mm adjacent to a predetermined point within said myocardium; and means for differencing cardiac signals sensed by said at least one pair of orthogonal electrodes to generate an electrographic signal indicative only of localized cardiac activity only within 1 to 3 mm of said predetermined point in said myocardium, said means for differencing cardiac signals being coupled to said at least one pair of orthogonal electrodes; and an ablative electrode disposed on said catheter for applying energy through said ablative electrode to extirpate myocardium in contact with said ablative electrode;

wherein said orthogonal electrodes are disposed within said ablative electrode, said orthogonal electrodes and means for differencing cardiac signals being arranged and adapted for simultaneously sensing only said localized cardiac activity of said myocardium at said predetermined point while said myocardium in contact with said ablative electrode is being extirpated, whereby said catheter is provided for ablating selected myocardium in said heart in response only to localized cardiac signals from myocardium at a specific spatial point.

8. A method for ablating myocardium of a heart comprising the steps of:

disposing a catheter within said heart at a position adjacent to a predetermined point in said myocardium;

sensing only localized cardiac signals from said myocardium within about 1 to 3 mm adjacent to said predetermined point without necessarily contacting said myocardium; and applying energy through said catheter to an ablative electrode at said predetermined point for the purpose of ablating myocardium at said predetermined point, where said step of sensing is performed by orthogonal electrodes disposed in said ablative electrode.

9. A method for ablating myocardium of a heart comprising the steps of:

disposing a catheter within said heart at a position adjacent to a predetermined point in said myocardium;

sensing only localized cardiac signals from said myocardium within about 1 to 3 mm adjacent to said predetermined point without necessarily contacting said myocardium; and applying energy through said catheter to an ablative electrode at said predetermined point for the purpose of ablating myocardium at said predetermined point, where said step of sensing is performed by orthogonal electrodes disposed in said ablative electrode within 1 to 5 millimeters from said distal tip.

10. A method for ablating myocardium of a heart comprising the steps of:

disposing a catheter within said heart at a position adjacent to a predetermined point in said myocardium;

sensing only localized cardiac signals from said myocardium within about 1 to 3 mm adjacent to said predetermined point without necessarily contacting said myocardium; and applying energy through said catheter to an ablative electrode at said predetermined point for the purpose of ablating myocardium at said predetermined point, where said step of sensing is performed by orthogonal electrodes disposed in said ablative electrode, and wherein said ablative electrode has cutouts defined therein and wherein said orthogonal electrodes are disposed in said catheter within said cutouts.

11. A method for ablating myocardium of a heart comprising the steps of:

disposing a catheter within said heart at a position adjacent to a predetermined point in said myocardium;

sensing only localized cardiac signals from said myocardium within about 1 to 3 mm adjacent to said predetermined point without necessarily contacting said myocardium; and applying energy through said catheter to an ablative electrode at said predetermined point for the purpose of ablating myocardium at said predetermined point, where said step of sensing is performed by orthogonal electrodes disposed in said ablative electrode, wherein said ablative electrode has cutouts defined therein, and wherein said orthogonal electrodes are disposed on said catheter and extend through said cutouts.

* * * * *